United States Patent [19]

Holtz

[11] 4,065,511

[45] Dec. 27, 1977

[54] ALCOHOL PRODUCTION

[75] Inventor: Hans D. Holtz, Bartlesville, Okla.

[73] Assignee: Phillips Petroleum, Bartlesville, Okla.

[21] Appl. No.: 399,491

[22] Filed: Sept. 21, 1973

Related U.S. Application Data

[63] Continuation-in-part of Ser. No. 315,824, Dec. 18, 1972, abandoned.

[51] Int. Cl.$^2$ .................. C07C 29/00; C07C 121/34; C07C 67/00
[52] U.S. Cl. .............................. 260/635 R; 260/465.6; 260/617 C; 260/618 H; 260/631 R; 260/631.5; 260/632 R; 560/145; 560/198
[58] Field of Search ........... 260/632 R, 635 R, 617 C, 260/618 H, 631.5, 631 R, 465.6, 479 R, 484 R

[56] References Cited

U.S. PATENT DOCUMENTS 3,476,816  11/1969  Farrissey .......................... 260/617 R

OTHER PUBLICATIONS

Lange, "Handbook of Chemistry" 10th ed. (1961), pp. 712–713.
Copley et al., "Proc. Chem. Soc.," (1964), pp. 300–301.
Jarvie et al., "Journal of Polymer Science": Part A-1, vol. 9, (1971), pp. 3105–3114.
Denney et al., "J. Am. Chem. Soc.," (1964), vol. 86, pp. 4487–4488.

Primary Examiner—Joseph E. Evans

[57] ABSTRACT

Selected organic peroxides are converted to the corresponding alcohols when contacted with a triorganophosphine in a reaction medium comprising water and an organic solvent miscible with water. In one embodiment, diene polyperoxides are converted to the novel diols.

14 Claims, No Drawings

ALCOHOL PRODUCTION

This is a continuation-in-part application of my application having Ser. No. 315,824, filed Dec. 18, 1972, entitled "Alcohol Production," and now abandoned.

BACKGROUND OF THE INVENTION

This invention relates to the production of alcohols. In one aspect, this invention relates to the production of alcohols by the reaction of selected organic peroxides, including polyperoxides and cyclic peroxides, with a triorganophosphine. In another aspect, this invention relates to a process for converting selected organic peroxides to alcohols in a reaction medium comprising water and organic solvents miscible with water. In a further aspect, this invention relates to the production of novel diols from diene polyperoxides.

The reaction of an organic peroxide with a triorganophosphine to yield an alcohol is known to the prior art. However, the alcohol is obtained as a mixture with an ether corresponding to the peroxide from which it is obtained. The ether may even be the major or sole product. This leads to separation and recovery of product problems which render the prior art processes unattractive commercially.

SUMMARY OF THE INVENTION

It is an object of this invention to provide an improved process for producing alcohols.

It is yet another object of this invention to provide a process for eliminating the formation of ethers in the production of alcohols.

It is another object of this invention to produce novel alcohols.

Other objects, aspects and the several advantages of the invention will be apparent to those skilled in the art from a study of the disclosure and the appended claims.

In accordance with these objects, I have found that, surprisingly, when a reaction medium comprising water and an organic solvent miscible with water is employed for the contacting of selected organic peroxides with a triorganophosphine, an alcohol, uncontaminated by ether formation, is obtained.

DESCRIPTION OF THE PREFERRED EMBODIMENTS

In accordance with one embodiment of this invention, selected organic peroxides are contacted with a triorganophosphine in a reaction medium comprising water and an organic solvent miscible with water. The product obtained is an alcohol free of an ether impurity.

In accordance with another embodiment of this invention, novel alcohols are produced from diene polyperoxides contacted with a triorganophosphine in a reaction medium comprising water and an organic solvent miscible with water.

In accordance with a further embodiment of this invention, novel alcohols comprising 2-octene-1,4-diol, 3-octene-1,2-diol, and 1-octene-3,4-diol are produced from 1,3-octadiene polyperoxide by contacting with triphenylphosphine in aqueous acetone as a reaction medium.

Generally, any triorganophosphine can be employed in the process of this invention. Although trihydrocarbylphosphines are preferred, trihydrocarbylphosphines substituted with other functional groups may be employed so long as they do not deleteriously affect the reaction.

Trihydrocarbylphosphines presently preferred for use in this invention include those of the formula $R_3P$ wherein R is a hydrocarbyl group. Suitable hydrocarbyl groups include groups selected from alkyl, aryl, cycloalkyl, alkaryl, aralkyl, and the like. Because of their ready availability, most preferred are those R groups having 1 to 12 carbon atoms. The R groups can be the same or different. During the course of the reaction the phosphine is converted to the corresponding oxide having the formula $R_3PO$ wherein R is as defined above.

Examples of suitable phosphines include trimethylphosphine, tri-p-tolylphosphine, tri-m-tolylphosphine, tricyclopentylphosphine, dicyclohexylethylphosphine, tribenzylphosphine, butylethylmethylphosphine, diethylphenylphosphine, tri-n-dodecylphosphine, 2-octyldimethylphosphine, tri-(2-cyclohexylethyl)phosphine, tri(3-ethylcyclohexyl)phosphine, triethylphosphine, tri-n-butylphosphine, tri-n-octylphosphine, triphenylphosphine, and the like.

One group of peroxides useful in this invention have the formula

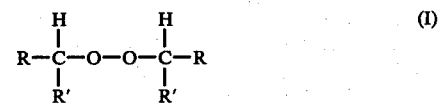

in which the R and R' groups can be the same or different and are selected from hydrogen and hydrocarbyl groups wherein the hydrocarbyl groups can be alkyl, cycloalkyl, aryl, and the like. Preferably, the R and R' groups will contain 1–12 carbon atoms. Examples of such peroxides include dimethyl peroxide, diethyl peroxide, diisopropyl peroxide, dibenzyl peroxide, di-n-butyl peroxide, di-n-hexyl peroxide, di-2-octyl peroxide, diisoamyl peroxide, didodecyl peroxide, bis(cyclohexylmethyl) peroxide, and the like. Such peroxides yield alcohols of the formula

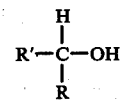

wherein R and R' are as defined above.

Cycloalkyl peroxides closely related to those described above are also useful in the process of this invention. Suitable cycloalkyl peroxides include those of the formula

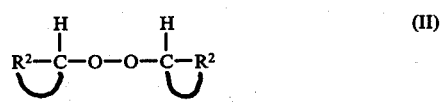

wherein $R^2$ is a divalent hydrocarbyl moiety. Preferably $R^2$ is an alkylene group having 3–9 carbon atoms. Examples of such peroxides are dicyclopentyl peroxide, dicyclohexyl peroxide, dicyclodecyl peroxide, di-3-methylcyclopentyl peroxide, di-4-butylcyclohexyl peroxide, and the like. Such peroxides yield alcohols of the formula

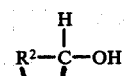

wherein $R^2$ is as defined above.

Yet another group of peroxides useful in this invention are the alicyclic peroxides of the formula

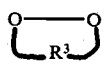
(III)

wherein $R^3$ is a hydrocarbyl group and preferably is an alkylene group containing 3–10 carbon atoms. Examples of suitable alicyclic peroxides are 1,2-dioxacyclohexane, 1,2-dioxacyclooctane, 1,2-dioxacyclopentane, 1,2-dioxacyclodecane, 1,2-dioxacyclododecane, and the like. Such peroxides yield diols of the formula HO — $R^3$ — OH wherein $R^3$ is as defined above.

Endoperoxides are also suitable for use in this invention. Suitable endoperoxides are prepared by the interaction of singlet oxygen in a Diels-Alder fashion with cyclic 1,3-dienes. Presently preferred are the endoperoxides of cyclopentadiene (A), 1,3-cyclohexadiene (B), and alpha-terpinene (C). The structures of these peroxides and the alcohol obtained therefrom are given below. The compound described by structure (C) is known as ascaridole.

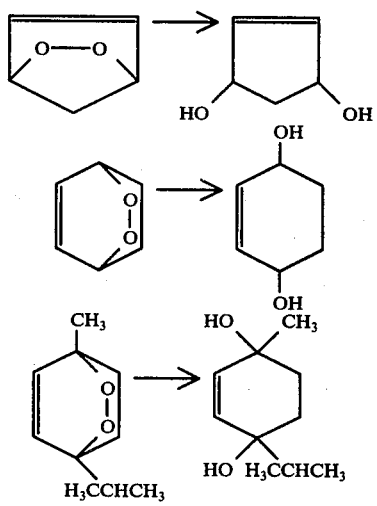

(A)

(B)

(C)

A further group of peroxides suitable for use in this invention are the organic polyperoxides. Suitable polyperoxides are normally derived from the free radical polymerization of olefinically unsaturated monomers in the presence of oxygen. Presently preferred polyperoxides derived from hydrocarbon monomers are those obtained from conjugated diolefins. Conjugated diolefins give rise to a mixture of peroxides having repeating units of the types

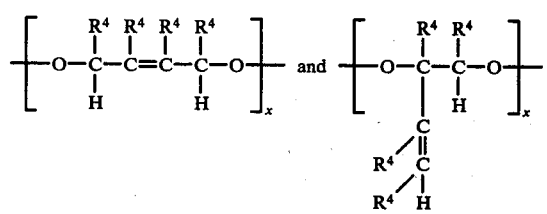

wherein $R^4$ can be the same or different and can be hydrogen or a hydrocarbyl moiety preferably selected from the group consisting of alkyl, aryl, and combinations thereof such as aralkyl, alkaryl, and the like, containing 2–20 carbon atoms, and x is an integer from 2 to 200. Suitable conjugated diolefins from which polyperoxides can be obtained include 1,3-butadiene, 1,3-octadiene, isoprene, piperylene, 2,3-dimethyl-1,3-butadiene, and the like. Such peroxides yield diols of the formulae

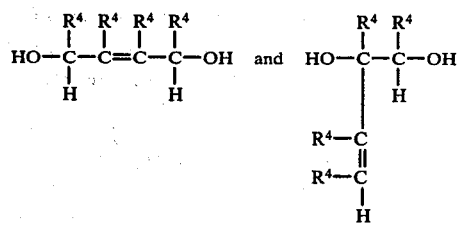

wherein $R^4$ is as defined above.

Other monomers from which polyperoxides can be derived include olefins conjugated with other functional groups such as cyano, aryl, aryloxycarbonyl, and alkyloxycarbonyl groups, and the like. The peroxides have repeating units of the type

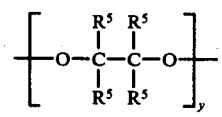

wherein y is an integer from 2–200 and $R^5$ can be the same or different and selected from hydrogen, alkyl, cycloalkyl, alkaryl, and the like, but at least one $R^5$ must be cyano, aryl, aryloxycarbonyl, alkyloxycarbonyl, or other functional group conjugated with the olefin prior to formation of the polyperoxide. Such peroxides yield diols of the formula

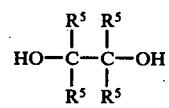

wherein $R^5$ is as defined above. Suitable olefin precursors to the polyperoxides include acrylonitrile, methacrylonitrile, styrene, indene, 1,1-diphenylethylene, methyl acrylate, butyl acrylate, phenyl acrylate, methyl methacrylate, and the like.

Water-soluble organic solvents suitable for use in the process of this invention should be able to solubilize the phosphine and the peroxide. Examples of such solvents are lower alkanones such as acetone and butanone-2, tetrahydrofuran, 1,4-dioxane, and the like.

The molar ratio of the phosphine to peroxide can vary over a wide range. However, at least one mole of phosphine should be provided for every equivalent of the peroxide. Polyperoxides, of course, contain more than one equivalent of peroxide per mole. A ratio of moles of phosphine to equivalents of peroxide greater than one is preferred. The reaction rate is increased by increasing the phosphine/peroxide ratio. Preferably the ratio will vary from about 1 to 5.

The molar ratio of water to equivalents of peroxide can also vary over a wide range. At least one mole of water per equivalent of peroxide is required to insure that no ether by-product is formed. However, too great an amount of water will cause the reaction medium to separate into two phases. This should be avoided. Therefore, the amount of water used should not exceed the amount which will cause phase separation. This amount is readily determined by routine experimentation for each peroxide used. Generally a ratio of from about 1 to 50 moles of water per equivalent of peroxide will be satisfactory. Preferably the ratio will be from about 1 to 10.

The temperature at which the process is carried out can vary over a wide range, being dependent upon the nature of the peroxide, concentration of reactants, and the like. Temperatures from about 0° C to 100° C are usually suitable. For convenience, temperatures from about room temperature (20° C) to about 60° C are preferred.

The reaction is best carried out in reactors capable of withstanding pressures to 20 atmospheres. Sealed pressure tubes and bomb type reactors are preferred for this purpose. The pressure at which the reaction is run should be sufficient to maintain the reaction substantially in the liquid phase. This will vary according to the reaction temperature and can be readily ascertained by routine experimentation. Pressures in the range from 0.5 to about 10 atmospheres are generally suitable. For convenience, it is preferred to employ pressures above about 1 atmosphere.

The reaction should be conducted in the substantial absence of oxygen. Therefore, an atmosphere of nitrogen, methane, or a nobel gas such as helium, argon, neon, xenon, or krypton or other gas inert to the reactant under the conditions employed should be maintained.

The reaction time can vary according to the nature of reactants and conditions employed. Generally, several hours to several days will be sufficient. For most reactants, 2–24 hours will be sufficient.

SPECIFIC EXAMPLES

Solutions of styrene polyperoxide and 1,3-octadiene polyperoxide for use in the present invention (see Examples I, II and III) were prepared by the following general procedure.

GENERAL PROCEDURE FOR POLYPEROXIDE PREPARATION

An approximately 0.01 molar solution of AIBN initiator [asobisisobutyronitrile; 2,2'-azobis(2-methylpropionitrile)] in freshly distilled monomer (e.g., styrene or 1,3-octadiene) was prepared in a volumetric flask. Aliquots of the AIBN/monomer solution were placed in a tared Pyrex bulb, the bulb was weighed, and attached to a stainless steel line connected to an oxygen reservoir. The glass bulb was placed in a 50° C temperature bath, flushed twice with oxygen and then pressured to about 70 psig oxygen. The oxygen pressure drop indicative of polyperoxide formation was monitored by means of a test gauge (to the nearest 0.1 psig), and the oxidation was continued until a suitable quantity of oxygen had been absorbed. After cooling to room temperature, the reactor bulb was vented, and weighed to determine oxygen uptake. This dilute solution (5–15 weight percent of monomer converted) of polyperoxide was stored in a brown bottle in a refrigerator at −10° C until used in the phosphine reductions of the present invention.

EXAMPLE I

A $1.22 \times 10^{-2}$ molar solution of AIBN in styrene was prepared by dissolving 0.1001 g AIBN (azobisisobutyronitrile) in 50 ml (45.3952 g) of freshly distilled styrene. A 45 ml aliquot of this solution (containing 41.7708 g styrene and 0.0921 g AIBN) was placed in a glass reactor bulb and oxidized as described above. A weight gain of 1.3879 g oxygen was observed corresponding to a pressure drop of 67.9 to 16.9 psig $O_2$ in a reaction period of 940 minutes. This indicates a 10.8 percent conversion of styrene to styrene polyperoxide assuming one mole of oxygen uptake per mole of styrene.

A 2.06 g sample of the above styrene polyperoxide solution ($2.06 \times 10^{-3}$ mole styrene polyperoxide based on oxygen uptake), 0.9971 g ($3.80 \times 10^{-3}$ mole) triphenylphosphine, 4 ml acetone, and 0.25 ml water were sealed under nitrogen in a pressure tube and the mixture was kept at room temperature for approximately 24 hours. Quantitative glc analysis of the reaction mixture gave the following results:

| Components | Mole |
| --- | --- |
| styrene glycol | $1.72 \times 10^{-3}$ |
| triphenylphosphine oxide | $1.96 \times 10^{-3}$ |

This represents a 95.1 mole percent yield of triphenylphosphine oxide based on polyperoxide, and 87.8 mole percent yield of styrene glycol based on triphenylphosphine oxide. The presence of styrene glycol in the reaction mixture was verified by trapping the appropriate effluent glc peak and recrystallizing the material from carbon tetrachloride. The recrystallized sample exhibited an infrared spectrum identical to that of authentic phenyl-1,2-ethanediol (styrene glycol). The recrystallized sample melted at 64° C (lit. m.p. for styrene glycol is 67°–68° C).

EXAMPLE II

A 2.0 g ($2.0 \times 10^{-3}$ mole styrene polyperoxide based on oxygen uptake) sample of the styrene polyperoxide solution prepared in Example I was mixed with 4 ml benzene and 1.0014 g triphenylphosphine in a sealed pressure tube under a nitrogen atmosphere. The mixture was kept at room temperature for 16 hours and quantitative glc analysis of the reaction mixture gave the following results:

| Components | Mole |
| --- | --- |
| styrene oxide | $1.16 \times 10^{-3}$ |
| triphenylphosphine oxide | $2.00 \times 10^{-3}$ |

This represents a 100 mole percent yield of triphenylphosphine oxide based on polyperoxide, and 58 mole percent yield of styrene oxide based on triphenylphosphine oxide.

EXAMPLE III

An approximately $1 \times 10^{-2}$ molar solution of AIBN in 1,3-octadiene was prepared by dissolving 0.0968 g AIBN (azobisisobutyronitrile) in 37.6705 g of freshly distilled c,t-1,3-octadiene. A 37.4050 g portion of this solution was placed in a glass reactor bulb and oxidation was carried out as described above. An oxygen uptake of 1.0258 g ($3.20 \times 10^{-2}$ mole) was observed. This indicates a 9.5 percent conversion of 1,3-octadiene to 1,3-octadiene polyperoxide assuming one mole oxygen uptake per mole of 1,3-octadiene.

Duplicate 2.000 g samples (A) and (B) of the above 1,3-octadiene polyperoxide solution were treated in sealed pressure tubes with an aqueous acetone solution of triphenylphosphine at room temperature for a period of 72 hours. Each reaction mixture contained 6 ml acetone and 0.25 ml water. Reaction mixtures from samples (A) and (B), respectively, also contained 1.0051 g triphenylphosphine, 0.2088 g benzophenone (internal glc standard); and 1.0018 g triphenylphosphine, 0.1970 g benzophenone (internal glc standard). Quantitative glc analysis of the reaction mixtures gave the following results (mole × $10^{-3}$):

| Components | Reaction Mixture from Sample A | from Sample B |
| --- | --- | --- |
| triphenylphosphine oxide | 1.61 | 1.54 |
| 2-octene-1,4-diol | 0.76 | 0.76 |
| 3-octene-1,2-diol | 0.35 | 0.33 |
| 1-octene-3,4-diol | 0.12 | 0.10 |

These results represent, respectively, 76 and 77 mole percent yields of glycols based on triphenylphosphine oxide in samples (A) and (B). The triphenylphosphine oxide data show, respectively, for samples (A) and (B), 97 mole percent and 93 mole percent yields based on polyperoxide.

The diol structures were verified by a combination of mass, infrared, and nuclear magnetic resonance analyses. The same diols were produced by reduction of the 1,3-octadiene polyperoxide by $NaAlH_2(OCH_2CH_2OCH_3)_2$. In addition, 3-octene-1,2-diol and 1-octene-3,4-diol were synthesized by reaction of 1,3-octadiene with m-chloroperbenzoic acid and hydrolysis of the epoxide and glycol ester.

The diols prepared in Example III are novel compositions of matter and the following data are given in support of structural assignments cited above:

a. 2-octene-1,4-diol-ir 3300, 2900, 1460, 1075, 1010, 975 $cm^{-1}$; mass spectrum m/e 113 ($M-CH_2OH$), 85 ($C_5H_9O.+$), 69 ($HO-CH=CH-CH=CH.+$), $$57\left(\begin{array}{c}CH_2-CH=CH-CH-C_4H_9\\ |\quad\quad\quad\quad\quad\quad |\\ OH\quad\quad\quad\quad\quad OH\end{array}\right),$$

31($CH_2-OH.+$); nmr($CDCl_3T60$) $\delta 0.85$(m,3H,methyl), 1.4(m,6H, methylene), 3.5 (S,2H,—OH), 4.1(m,3H,methine plus methylene), 5.8 (m,2H, nonterminal olefinic).

b. 3-octene-1,2-diol-ir 3300, 2900, 1450, 1065, 1025, 970, 875 $cm^{-1}$; mass spectrum m/e 144 ($M+C_8H_{16}O_2$), 113($M-CH_2OH$), 95(m/e 113—$H_2O$), 69;

57(HO—$CH_2$—CH(OH)—CH—$C_3H_7$ ⇌ HO—$CH_2$—CH=CH—CH=CH—$C_3H_7$);
57                                                        69 nmr($CDCl_3$) $\delta 0.9$(m,3H,methyl), 1.4(m,4H,methylene), 2.0(m,2H, $CH_2$—C=C—), 3.6(m,4.1H,OH,$CH_2$ next to OH), 4.2 (1H,methine), 5.6(m,1.9H nonterminal olefin).

c. 1-octene-3,4-diol-ir 3300, 2900, 1450, 1100, 1030, 990, 920, 830 $cm^{-1}$; mass spectrum m/e 87 (HO—CH—$C_4H_9.+$), 69(m/e 87—$H_2O$), 58 (base peak), 57($CH_2=CH-CH-OH.+$); nmr($CDCl_3$) $\delta 0.9$(m,3H,methyl), 1.3(5.9H,methylene), 2.4(2.3H,—OH), 3.6(1H, methine adj. to OH), 4.0(1H,methine), 5-6(2.8H, vinyl).

EXAMPLE IV

A 0.209 g (1.03 × $10^{-3}$ mole) sample of di-n-hexyl peroxide, 0.385 g (1.90 × $10^{-3}$ mole) tri-n-butylphosphine, 8 ml acetone, and 0.4 ml water were sealed under nitrogen in a pressure tube at room temperature for approximately 72 hours. Quantitative glc analysis of the reaction mixture gave the following results:

| Components | Moles |
| --- | --- |
| n-hexanol | 2.0 × $10^{-3}$ |
| tri-n-butylphosphine oxide | 1.08 × $10^{-3}$ |

This represents ca. 100 mole percent yield of tri-n-butylphosphine oxide based on di-n-hexyl peroxide, and ca. 100 mole percent yield of n-hexanol based on di-n-hexyl peroxide.

EXAMPLE V

A 0.088 g (1.00 × $10^{-3}$ mole) sample of 1,2-dioxane, 0.380 g (1.88 × $10^{-3}$ mole) tri-n-butylphosphine, 8 ml acetone and 0.4 ml water were sealed under nitrogen in a pressure tube at room temperature for approximately 168 hours. Quantitative glc analysis of the reaction mixture gave the following results:

| Components | Moles |
| --- | --- |
| 1,4-butanediol | 0.88 × $10^{-3}$ |
| tri-n-butylphosphine oxide | 0.91 × $10^{-3}$ |

This represents a 91 mole percent yield of tri-n-butylphosphine oxide based on 1,2-dioxane, and 88 mole percent yield of 1,4-butanediol based on 1,2-dioxane.

EXAMPLE VI

A 0.69 g (4.10 × $10^{-3}$ mole) sample of ascaridole, 1.28 g (6.36 × $10^{-3}$ mole) tri-n-butylphosphine, 6 ml acetone, and 0.25 ml water were sealed under nitrogen in a pressure tube at 75° C for approximately 24 hours. Quantitative glc analysis of the reaction mixture gave the following results:

| Components | Moles |
| --- | --- |
| tri-n-butylphosphine oxide | 3.59 × $10^{-3}$ |

| Components | Moles |
|---|---|
| p-menthene-1,4-diol | $1.29 \times 10^{-3}$ |

This represents an 88 mole percent yield of tri-n-butylphosphine oxide based on ascaridole, and 31 mole percent yield of p-menthene-1,4-diol based on ascaridole.

The alcohols and diols prepared according to this invention find utility in a number of applications. Diols can be used in the preparation of polyesters, a class of polymers having well-known properties.

The simple alcohols can be used in the preparation of esters of carboxylic acids for a variety of purposes. High molecular weight esters are useful as plasticizers for polymeric materials. Other utilities of the alcohol products from this invention will be apparent to one of skill in the art.

The following example directed to di-tert-butyl peroxide illustrates that this peroxide is not suitable for use in the present process.

EXAMPLE VII

A 90 mg ($1 \times 10^{-3}$ mol) sample of di-tert-butyl peroxide, $1.97 \times 10^{-3}$ mol tri-n-butyl phosphine, 8 ml acetone and 0.4 ml water were sealed under nitrogen in a pressure tube at 50° C for a period of 10 days. Gas chromatographic analysis of the reaction mixture showed no tert-butyl alcohol or di-tert-butyl ether. A similar run was carried out at room temperature and no detectable amounts of either tert-butyl alcohol or di-tert-butyl ether were found.

I claim:
1. A process for preparing alcohols substantially free of ethers which comprises contacting at a temperature in the range of from about 0° C to 100° C, a pressure in the range from 0.5 to about 10 atmospheres, and under an atmosphere which is substantially free of oxygen:
   a. at least one organic peroxide selected from:
   I. organic peroxides having the formula

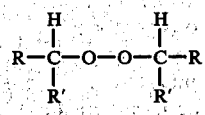

wherein R and R' are hydrocarbyl groups selected from alkyl, cycloalkyl, and aryl groups having from 1-12 carbon atoms,
   II. organic peroxides having the formula

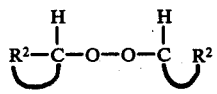

wherein $R^2$ is an alkylene group having 3-9 carbon atoms,
   III. organic peroxides having the formula

wherein $R^3$ is a hydrocarbyl group having from 3-10 carbon atoms,
   IV. endoperoxides, and
   V. polyperoxides derived from the free radical polymerization of olefinically unsaturated monomers in the presence of oxygen and wherein the olefinically unsaturated monomer is
   1. a conjugated diene and the polyperoxide has repeating units of the formulas

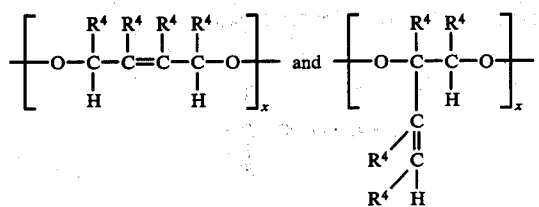

wherein x is an integer from 2 to 200 and $R^4$ is hydrogen or a hydrocarbyl group selected from the group consisting of alkyl, aryl, alkaryl, aralkyl, and alkaryl groups having 2-20 carbon atoms, or
   2. olefins conjugated with other functional groups selected from cyano, aryl, aryloxycarbonyl, and alkyloxycarbonyl groups and the polyperoxide has repeating units of the formula

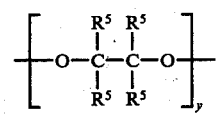

wherein y is an integer from 2-200 and $R^5$ is selected from hydrogen, alkyl, cycloalkyl, aryl, alkaryl, cyano, aryloxycarbonyl, and alkyloxycarbonyl groups with the proviso that at least one $R^5$ must be cyano, aryl, aryloxycarbonyl, alkyloxycarbonyl, or other functional group conjugated with the olefin prior to formation of the polyperoxide, with
   b. a trihydrocarbylphosphine wherein the hydrocarbyl group has from 1 to 12 carbon atoms, the molar ratio of phosphine to equivalents of peroxide being at least 1, and
   c. a reaction medium comprising water and a water-soluble organic solvent selected from lower alkanones, tetrahydrofuran, and 1,4-dioxane also capable of solubilizing the phosphine and peroxide, the amount of water present being at least one mole of water per equivalent of peroxide which is sufficient to insure that no ether by-product is formed but the amount of water should not exceed the amount which will cause the reaction medium to separate into two phases.

2. A process according to claim 1 wherein the temperature is in the range of 20°-60° C and the molar ratio of water to equivalents of peroxide is about 1-50.

3. A process according to claim 1 wherein the atmosphere is selected from nitrogen, methane, or a noble gas, the molar ratio of phosphine to equivalents of peroxide varies from about 1-5, and the molar ratio of water to equivalents of peroxide varies from about 1-10.

4. A process according to claim 1 wherein the organic solvent is acetone, butanone-2, tetrahydrofuran, or 1,4-dioxane.

5. A process according to claim 1 wherein the peroxide is di-n-hexyl peroxide, 1,2-dioxane, ascaridole, styrene polyperoxide, or 1,3-octadiene polyperoxide.

6. A process according to claim 1 wherein the triorganophosphine is selected from triphenylphosphine and tri-n-butylphosphine.

7. A process according to claim 1 wherein the peroxide has a formula selected from

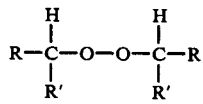 (I)

wherein R and R' are hydrocarbyl groups selected from alkyl, cycloalkyl, and aryl groups having from 1-12 carbon atoms,

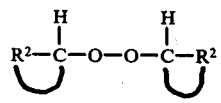 (II)

wherein $R^2$ is an alkylene group having 3-9 carbon atoms, and

 (III)

wherein $R^3$ is an alkylene group having 3-10 carbon atoms.

8. A process according to claim 1 wherein the peroxide is an endoperoxide of a cyclic 1,3-diene selected from the group consisting of cyclopentadiene, 1,3-cyclohexadiene, and alpha-terpinene.

9. A process according to claim 1 wherein the peroxide is a polyperoxide derived from the free radical polymerization of olefinically unsaturated monomers in the presence of oxygen and wherein the olefinically unsaturated monomer is (1) a conjugated diene and the polyperoxide has repeating units of the formulas

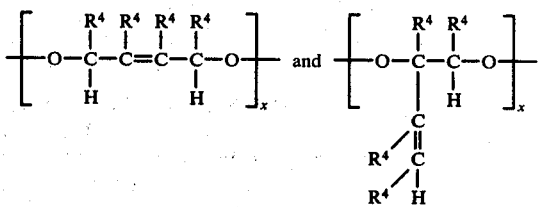

wherein $x$ is an integer from 2 to 200 and $R^4$ is hydrogen or a hydrocarbyl group selected from the group consisting of alkyl, aryl, alkylaryl, aralkyl, and alkaryl groups having 2-20 carbon atoms, or (2) an olefin conjugated with other functional groups selected from cyano, aryl, aryloxycarbonyl, and alkyloxycarbonyl groups and the polyperoxide has repeating units of the formula

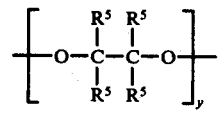

wherein $y$ is an integer from 2-200 and $R^5$ is selected from hydrogen, alkyl, cycloalkyl, aryl, alkaryl, cyano, aryloxycarbonyl, and alkyloxycarbonyl groups with the proviso that at least one $R^5$ must be cyano, aryl, aryloxycarbonyl, alkyloxycarbonyl, or other functional group conjugated with the olefin prior to formation of the polyperoxide.

10. A process according to claim 9 wherein the conjugated diene is 1,3-octadiene.

11. A process according to claim 9 wherein the olefinically unsaturated monomer is selected from conjugated nitriles, esters of conjugated acids, and vinyl aromatic compounds.

12. A process according to claim 11 wherein the unsaturated monomer is styrene.

13. A process according to claim 9 wherein 1,3-octadiene polyperoxide is contacted with triphenylphosphine in aqueous acetone.

14. A process according to claim 9 wherein styrene polyperoxide is contacted with triphenylphosphine or tri-n-butylphosphine in aqueous acetone.

* * * * *